United States Patent [19]

Hoegnelid

[11] Patent Number: 5,522,855
[45] Date of Patent: Jun. 4, 1996

[54] IMPLANTABLE CARDIAC STIMULATOR

[75] Inventor: Kurt Hoegnelid, Vaesterhaninge, Sweden

[73] Assignee: Siemens Elema AB, Solna, Sweden

[21] Appl. No.: 294,334

[22] Filed: Aug. 23, 1994

[30] Foreign Application Priority Data

Sep. 24, 1993 [SE] Sweden ................................. 9303121

[51] Int. Cl.$^6$ ................................................ A61N 1/368
[52] U.S. Cl. ............................................................ 607/9
[58] Field of Search ................................. 607/13, 9, 27, 607/28

[56] References Cited

U.S. PATENT DOCUMENTS 4,535,776  8/1985  Strandberg et al. .
4,543,956  10/1985  Herscovici .............................. 607/13
4,811,738  3/1989  Economides et al. .................... 607/13

*Primary Examiner*—William E. Kamm
*Assistant Examiner*—Kennedy J. Schaetzle
*Attorney, Agent, or Firm*—Hill, Steadman & Simpson

[57] ABSTRACT

An implantable cardiac stimulator has an atrial electrode for placement in the atrium of a heart and a ventricular electrode for placement in the ventricle of the heart. In order to sense stimulated events in the heart, a detector is connected to both of the electrodes to measure electrical heart signals between them.

10 Claims, 2 Drawing Sheets

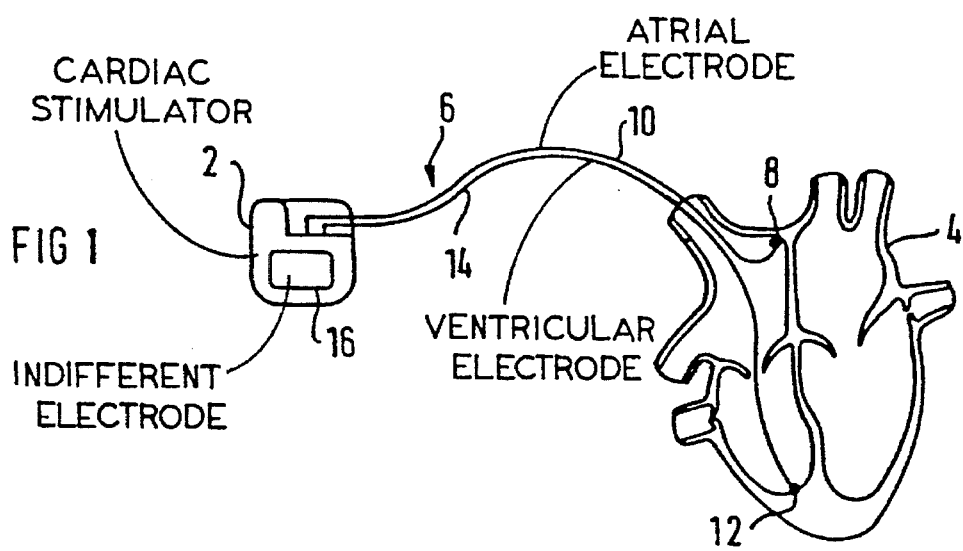
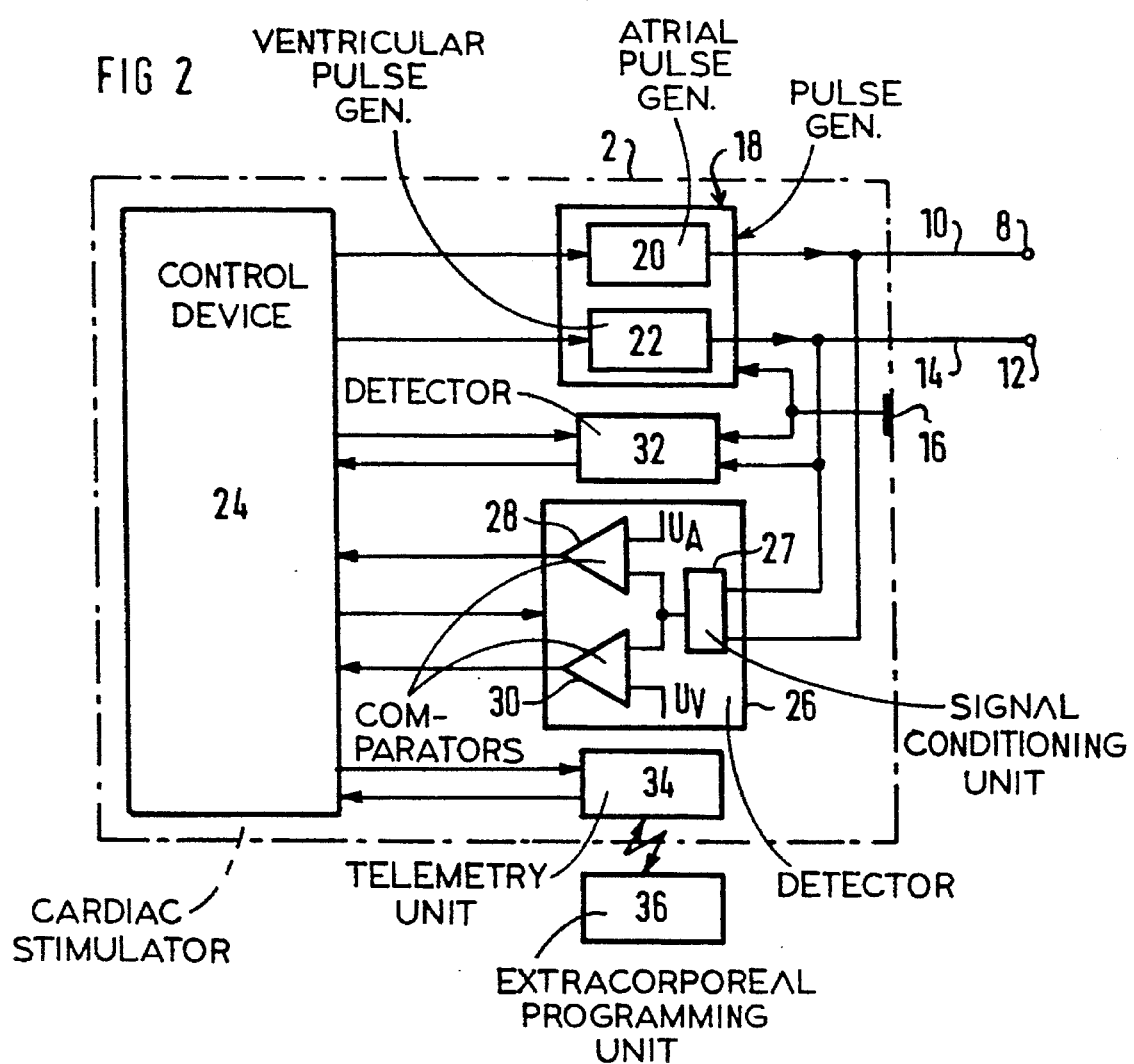

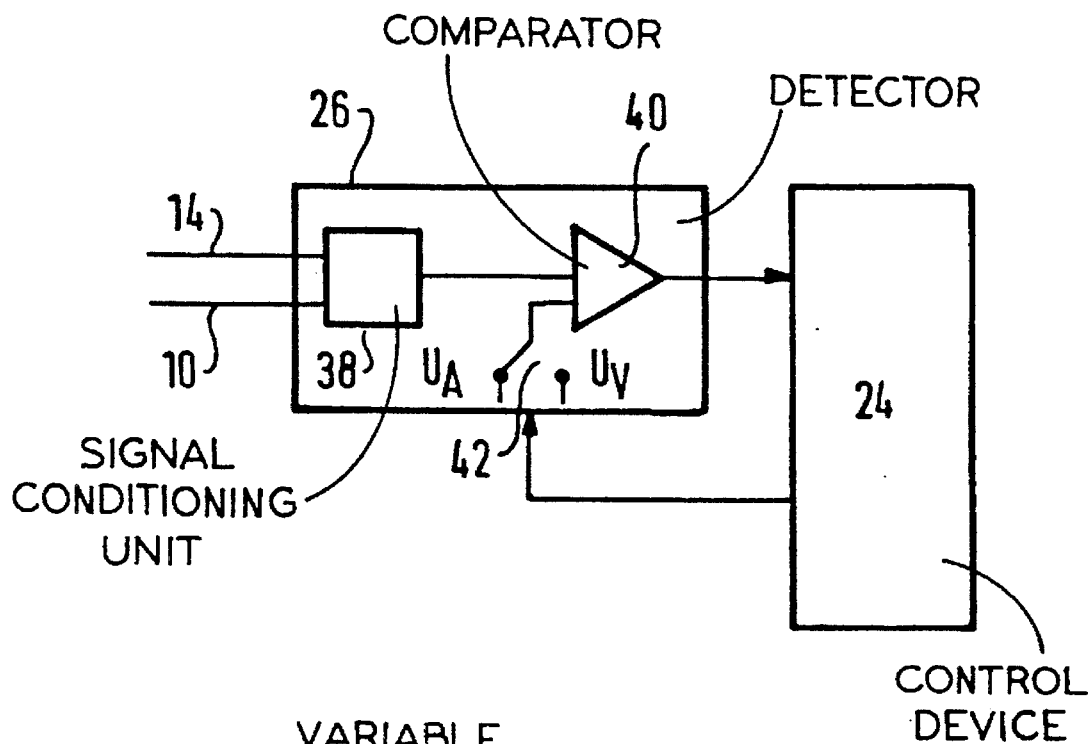
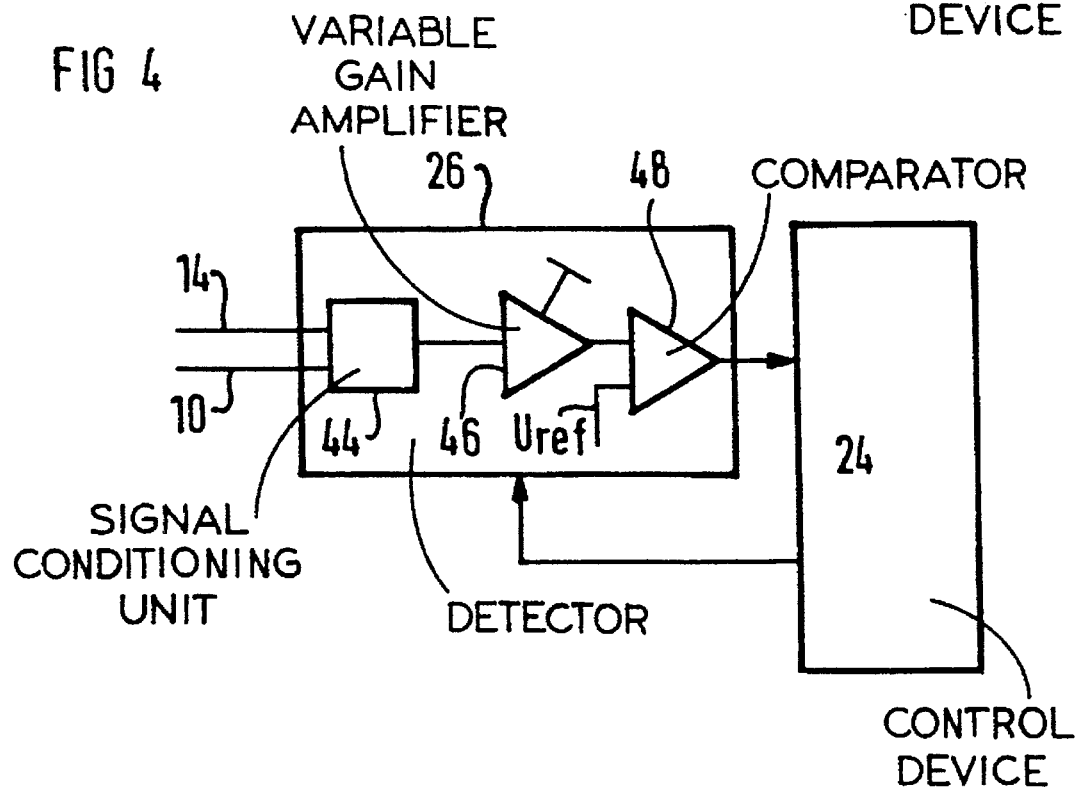

IMPLANTABLE CARDIAC STIMULATOR

BACKGROUND OF THE INVENTION

1. Field of the Invention

The present invention relates to a cardiac stimulator of the type having a pulse generator and an electrode system which includes an atrial electrode, arranged in an atrium of a heart, and a ventricular electrode, arranged in a ventricle of the heart, whereby stimulation pulses, generated by the pulse generator are supplied to the atrium via the artial electrode or to the ventricle via the ventricular electrode for stimulating a heart response.

2. Description of the Prior Art

In a dual chamber system of the above-described type, the atrium and ventricle can be stimulated in a synchronous sequence which emulates a natural heart cycle in a healthy heart. In order to prevent the release of needless stimulation pulses to the heart, the atrium and the ventricle can be sensed for spontaneous (natural) activity. For example, if the ventricle is sensed for spontaneous activity, ventricular stimulation pulses are inhibited when a spontaneous ventricular event (ventricular systole) is sensed. Such a system is designated DVI. The DVI-system is further refined the if the atrium is also sensed for spontaneous activity. A sensed spontaneous atrial event (atrial systole) would then inhibit emission of an atrial stimulation pulse. This refined system is known under the designation DDI. A heart stimulator is designated DDD if it is devised for both triggering and inhibiting according to spontaneous activity sensed in both the atrium and the ventricle.

European Application 0 308 536 describes a heart stimulator which can stimulate and sense both in the atrium and ventricle. This known cardiac stimulator has two electrodes in the atrium (atrial electrodes), two electrodes in the ventricle (ventricular electrodes) and an indifferent electrode, consisting of the cardiac stimulator's capsule. Stimulation and sensing of both the atrium and the ventricle can be achieved either between an electrode and the capsule or between the two electrodes in the respective chamber, i.e. atrial stimulation and sensing between one atrial electrode and the capsule or between two atrial electrodes, and ventricular stimulation and sensing between one ventricular electrode and the capsule or between two ventricular electrodes.

The electrodes are implanted in the heart on electrode leads. For this known cardiac stimulator, a bipolar electrode lead can be implanted in the atrium, and a bipolar electrode lead can be implanted in the ventricle. The electrode emitting the stimulation pulses must be in contact with heart tissue in order to stimulate that tissue. A sensing electrode, however, does not need to be in contact with heart tissue, since blood in the heart conducts current better than the tissue itself. It is nonetheless preferable to have even the sensing electrode in contact with heart tissue, since this will result in more distinct signals. This is because an electrode which is not in direct contact with tissue picks up signals from a large area of tissue. In addition, interference signals are conducted better in blood than in tissue and thus affect the measurement signal to a larger degree.

As an alternative to two bipolar electrode leads, a quadripolar electrode lead can be used, provided it is constructed so at least one of the two electrodes located in the atrium is in contact with heart tissue for stimulating same. The advantage of a quadripolar electrode lead is that it facilitates implantation, since only one electrode lead has to be introduced into the heart. The disadvantage of a quadripolar electrode lead is that it is thicker and stiffer than a bipolar electrode lead.

In European Application 0 596 319 (published after the filing of the prior Swedish application on which the present application is based), a cardiac stimulator which has an electrode system for sensing atrial and ventricular heart events is described. The electrode system has one atrial electrode, one ventricular electrode and an indifferent electrode, consisting of the heart stimulator's capsule. Ventricular events are sensed in the same way as in the above-described known cardiac stimulator, i.e. between the ventricular-electrode and the indifferent electrode. Spontaneous atrial activity is sensed between the atrial electrode and the ventricular electrode. With this design, the number of conductors in the electrode lead can be reduced compared to when a separate sensing electrode is used, as in the above-described known heart stimulator.

In order to operate as effectively as possible in the DDD mode, the cardiac stimulator should automatically ascertain whether emitted stimulation pulses result in any heart events, i.e. evoked responses. If provided with such a function, the heart stimulator will have an ability to automatically set the stimulation amplitude at a value which is as close to the heart's stimulation threshold value as possible, thereby saving energy. This function is known as autocapture.

One problem associated with the autocapture function is to distinguish between signals having different origins in the heart without the need for excessively comprehensive electronics or circuit logic. Cardiac stimulators are designed so as not to impede or disturb the patient receiving the heart stimulator. Therefore, the volume and weight of the heart stimulator are restricted as much as possible, and this naturally limits the possibility of incorporating comprehensive electronics in the stimulator.

SUMMARY OF THE INVENTION

An object of the present invention is to provide a cardiac simulator which can simply and safely detect spontaneous and evoked heart responses in a manner which avoids complex circuitry and thus allows the pulse generator and associated electronics to be contained in a capsule of a size and weight which are not disturbing to a patient in whom the cardiac stimulator is implanted.

Such a cardiac stimulator is achieved in accordance with the invention wherein a detector is connected both to the atrial electrode and to the ventricular electrode for sensing stimulated ventricular heart events.

In conjunction with the emission of a ventricular stimulation pulse, the detector is activated to sense the signal between the ventricular electrode and the atrial electrode. If a ventricular heart event is stimulated by the ventricular stimulation pulse, the electrical signal in the heart tissue (the depolarization signal) will be sensed, and the detector will generate a signal which indicates that an evoked response has occurred in the heart. Thus only two electrodes are used for sensing evoked ventricular heart events. As a result of differences in polarity and signal strength between atrial and ventricular signals. and, particularly differences in logic structure and function, a detector devised according to the known cardiac stimulator in European Application 0 596 319 is unable to detect any stimulated ventricular events, even though it can detect atrial events between an atrial electrode and a ventricular electrode. For example, the blanking functions, i.e., the time windows in which the detector does not sense any signals, are completely different.

It is advantageous if the cardiac stimulator according to the present invention includes a control device connected to the detector for activating the detector for a predetermined time window in conjunction with the pulse generator's emission of ventricular stimulation pulses, in order to sense stimulated ventricular heart events.

The detector can contain a special electronic circuit for conditioning (editing) the measurement signal after a ventricular stimulation pulse, this conditioning circuit being activated by a switch controlled by the logic circuit. In order to minimize space requirements, activation can be devised as a purely logical operation, i.e., a signal from the detector is accepted as an evoked response only if received in the predetermined time window. This is possible due to an understanding of the heart's physiology. A heart signal originates either in the or atrium or the ventricle. After an atrial event (spontaneous or stimulated), the atrium needs time to recover before a new atrial event (spontaneous or stimulated) can occur. The recovery time required (refractory period) varies, but it cannot be shorter, in principle, than the repolarization time of atrial heart cells. Under normal conditions, the heart beats at a rate of 70 to 150 beats a minute. Under normal conditions, atrial responses therefore occur at intervals which are never less than about 400 ms (150 bpm=2.5 Hz, which corresponds to 400 ms). Between these intervals the atrial electrode can be used as a reference for the ventricular electrode in the sensing signals. The time window is appropriately chosen as to minimize the effect in case of abnormal atrial activity.

In a further version of the cardiac stimulator in accordance with the invention, the detector also senses stimulated atrial heart events and in the aforementioned control device activates the detector in conjunction with every $n^{th}$ atrial stimulation pulse for sensing stimulated atrial heart events, n being a whole number, preferably between 1 and 6.

In order to ensure patient safety, each ventricular stimulation pulse should be checked to determine whether it stimulates a response. For the atrium, however, however, it is sufficient to check the stimulation pulse at regular intervals to make sure that the atrial stimulation pulses are still effective. For the atrium, activation of the detector can be performed physically by a switch or by a logic function.

In conjunction herewith, it is advantageous for the pulse generator to generate a biphasic atrial stimulation pulse or some other polarization-compensating stimulation pulse when a stimulated atrial event is to be sensed. The biphasic, or polarization compensating, stimulation pulse ensures that the atrial electrode does not acquire any residual polarization after the stimulation pulse is emitted. Detection of the stimulated event is thereby facilitated. The ventricular stimulation pulse can also be devised in a corresponding manner to facilitate detection of stimulated ventricular events.

In another version of the cardiac stimulator in accordance with the invention, the electrode system includes an indifferent electrode, located outside the heart, and a further detector is connected to the ventricular electrode and to the indifferent electrode for sensing spontaneous ventricular events, and the further detector is activated at the same time as the other detector is activated in order to sense stimulated atrial events.

If an abnormal ventricular event occurs, i.e., a ventricular extra systole (VES), it is advantageous if the heart stimulator is able to distinguish between a stimulated atrial event and a spontaneous VES. This is achieved by adding the further detector which senses the ventricle at the same time as atrial measurement is performed. The indifferent electrode can appropriately consist of the capsule (in part or whole). If both detectors sense an event, it cannot be determined that a stimulated event has occurred in the atrium. Sensing of the atrium should then be repeated.

In conjunction with sensing of atrial heart events after every $n^{th}$ atrial stimulation pulse, repetition of sensing is advantageously made after the next, consecutive atrial stimulation pulse when both detectors have sensed an event.

DESCRIPTION OF THE DRAWINGS

FIG. 1 is a schematic rendition of a stimulator connected to a heart.

FIG. 2 is a block diagram of a cardiac stimulator constructed in accordance with the principles of the present invention.

FIG. 3 shows a first alternative version of a detector for use in the cardiac stimulator of the invention.

FIG. 4 shows a second alternative version of a detector for use in the cardiac stimulator of the invention.

DESCRIPTION OF THE PREFERRED EMBODIMENTS

As shown in FIG. 1, a cardiac stimulator 2, such as the cardiac stimulator of the invention, is connected to a heart 4 by means of an electrode system 6. The electrode system 6 has an atrial electrode 8, which is arranged in the atrium of the heart 4. Via an atrial electrode connector 10, electrical signals can be carried between the atrial electrode 8 and the heart stimulator 2. Further, a ventricular electrode 12 is arranged in the ventricle of the heart 4, and electrical signals can be carried between the ventricular electrode 12 and the heart stimulator 2 via a ventricular electrode conductor 14. The heart stimulator 2 also has an indifferent electrode 16 which can consist of a part or all of the capsule of the heart stimulator 2.

In FIG. 2 the structure of the heart stimulator 2 is schematically shown in a block diagram. Both the atrial electrode 8 and the ventricular electrode 12 are connected to a pulse generator 18, via the atrial electrode conductor 10 and the ventricular electrode conductor 14. The pulse generator 18 generates and emits atrial stimulation pulses from an atrial pulse generator 20 and ventricular stimulation pulses from a ventricular pulse generator 22. Both the atrial pulse generator 20 and the ventricular pulse generator 22 are controlled by a control device 24. The control device 24 controls the shape, amplitude, duration, stimulation interval etc. of the stimulation pulses.

The indifferent electrode 16 is also connected to the pulse generator 18, in order to form a common return line for atrial and ventricular stimulation pulses delivered to the heart 4 via the atrial electrode 8 and the ventricular electrode 12 respectively. A stimulation pulse returns through body tissue via the indifferent electrode 16 to the pulse generator 18.

The atrial electrode 8 and ventricular electrode 12 are connected to a detector 26 via the atrial electrode conductor 10 and ventricular electrode conductor 14. The detector 26 includes a signal conditioning unit 27, an atrial comparator 28 and a ventricular comparator 30. Since ventricular depolarization signals are much stronger than atrial depolarization signals, two different reference signals are used for the comparators 28 and 30. Signal conditioning in the signal conditioning unit 27 can be identical for the signals from both the atrium and the ventricle and can include, e.g., signal filtering and amplification. The signal conditioning unit 27 can also be devised so that detected signals are filtered in different ways, depending on whether they have a spontaneous or stimulated origin. Stimulated events can only follow an emitted stimulation pulse, so devising the signal conditioning detector 27 to achieve this differential filtering is therefore no problem.

The output signal from the signal conditioning unit 27 is subsequently compared in the atrial comparator 28 with an atrial reference potential $U_A$. If the output signal is larger than the reference potential, a detection signal is sent from the atrial comparator 28 to the control device 24.

The logic of the control device 24, however, must be activated for receiving atrial events if the detection signal from the atrial comparator 28 is to be accepted as an atrial event.

In a corresponding manner, the output signal from the signal conditioning unit 27 is compared in the ventricular comparator 30 with a ventricular reference potential $U_V$. A detection signal from the ventricular comparator 30 is only accepted as a ventricular event if the logic of the control device 24 has been activated for receiving ventricular events.

The control device 24 also controls the detector 26. It determines, e.g., when the detectors 28 and 30 are to be activated and the sensitivity with which heart signals are to be sensed.

A further detector 32 is connected to the ventricular electrode 12 and the indifferent electrode 16 to sense spontaneous ventricular events in the heart.

In order to detect stimulated ventricular events, the control device 24 operates as follows: After an approved atrial event, spontaneous or evoked, the ventricle is sensed for a spontaneous ventricular event during a time period referred to as the A-V interval. If no spontaneous ventricular event is sensed during the A-V interval, the control device 24 orders the emission of a ventricular stimulation pulse. At the same time the logic of the control device 24 is activated to sense whether the ventricular comparator 30 emits a detection signal in the time window for which the logic is activated. If a ventricular event is sensed during the time window, evoked response is established. The control device 24 can then proceed and activate the logic for sensing a spontaneous atrial event. Otherwise, a new ventricular stimulation pulse, containing a higher energy than the last, must be delivered to the ventricle.

Atrial stimulation pulses are emitted when no spontaneous atrial stimulation pulse is sensed within an A-A interval from the last atrial event (spontaneous or stimulated). For the atrium, every stimulation pulse does not have to be checked for evoked response. Checking only, e.g., every third atrial stimulation pulse is fully sufficient. In order to facilitate detection of the weaker atrial signal, a biphasic stimulation pulse is delivered to the atrium. As a result, polarization of the electrode 8 does not persist too long. At the same time, the logic of the control device 24 is activated in order to identify a detection signal from the atrial comparator 28 as an atrial event. For safety, the further detector 32 is also activated during the same period of time. The further detector 32 ensures that no ventricular extra systoles are spuriously sensed as stimulated atrial events. The further detector 32 transmits detection signals to the control device 24 and receives control signals therefrom in the same way as the detector 26.

The heart stimulator 2 also contains a telemetry unit 34 which is connected to the control device 24 and which can talemetrically receive and transmit information to/from an extracorporeal programming unit 36. With the programming unit 36, a physician can, e.g., retrieve stored information from the control device 24 and even re-program the parameters of the heart stimulator 2.

FIG. 3 shows an alternative design for the detector 26 for detecting both atrial and ventricular signals. In a signal conditioning unit 38, input signals from the electrode conductors 10 and 14 are conditioned in the same way as in FIG. 2. In this instance, however, only one comparator 40 is used to compare the output signal with the reference potentials $U_A$ and $U_V$. A switch 42, controlled by the control device 24, connects the relevant reference potential at any given moment. In other words, the atrial reference potential $U_A$ is switched to the comparator 40 when atrial events are to be sensed, and the ventricular reference potential $U_V$ is switched to the comparator 40 when ventricular events are to be sensed.

FIG. 4 shows yet another version of the detector 26. After signal conditioning in a signal conditioning unit 44, the conditioned signal is sent to a variable amplifier 46. The gain of the variable amplifier 46 is controlled by the control device 24. The output signal from the amplifier 46 is then compared in a comparator 48 with a uniform reference potential $U_{ref}$. Depending on whether atrial or ventricular events are to be sensed, the control device 24 appropriately changes the gain of the variable amplifier 46.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable cardiac stimulator comprising:

a pulse generator contained in a housing adapted for implantation in a patient;

an electrode system including an atrial lead carrying an atrial electrode adapted for placement in the atrium of the heart of said patient and a ventricular lead carrying a ventricular electrode adapted for placement in the ventricle of said heart, said atrial electrode and said ventricular electrode being respectively electrically connected to said pulse generator via said atrial and ventricular leads for delivering atrial stimulation pulses to the atrium via said atrial electrode and ventricular stimulation pulses to the ventricle via said ventricular electrode for stimulating cardiac activity; and a detector contained in said housing and electrically connected to said atrial electrode and to said ventricular electrode for sensing stimulated ventricular cardiac events in said heart exclusively by detecting cardiac signals between said atrial electrode and said ventricular electrode.

2. An implantable cardiac stimulator as claimed in claim 1 further comprising control means contained in said housing and connected to said detector for activating said detector for a predetermined time window associated with the generation of a ventricular pulse by said pulse generator for sensing said stimulated ventricular cardiac events.

3. An implantable cardiac stimulator as claimed in claim 2 wherein said detector comprises means for sensing stimulated atrial cardiac events in said heart, and wherein said control means comprises means for activating said detector for each $n^{th}$ atrial stimulation pulse for sensing said stimulated atrial cardiac events, n being a whole number.

4. An implantable cardiac stimulator as claimed in claim 3 wherein said control means comprises means for activating said detector in conjunction with every $n^{th}$ atrial stimulation pulse with n being in a range between 1 and 6.

5. An implantable cardiac stimulator as claimed in claim 3 wherein said pulse generator comprises means for generating a polarization-compensating atrial stimulation pulse when a stimulated atrial event is to be sensed.

6. An implantable cardiac stimulator as claimed in claim 5 wherein said pulse generator comprises means for generating a biphasic atrial stimulation pulse when a stimulated atrial event is to be sensed.

7. An implantable cardiac stimulator as claimed in claim 3 wherein said electrode system comprises an indifferent electrode adapted to be disposed in said patient outside of said heart, and wherein said implantable cardiac stimulator comprises a further detector connected to said ventricular electrode and to said indifferent electrode for sensing spontaneous ventricular events by detecting cardiac signals between said ventricular electrode and said indifferent electrode, and wherein said control means comprises means for activating said further detector simultaneously with the activation of said means in said detector for sensing stimulated atrial events.

8. An implantable cardiac stimulator as claimed in claim 1 wherein said cardiac signals have an amplitude, and wherein said detector comprises:

first comparator means for comparing the amplitude of said cardiac signals to a predetermined atrial reference level and for emitting an output signal indicative of atrial electrical activity if said amplitude of said cardiac signals exceeds said predetermined atrial level;

second comparator means for comparing the amplitude of said cardiac signals to a predetermined ventricular reference level and for emitting an output signal indicative of ventricular electrical activity if said amplitude of said cardiac signals exceeds said predetermined ventricular reference level;

and wherein said implantable cardiac stimulator comprises control means connected to said pulse generator and to said detector for controlling said pulse generator dependent on the respective output signals of the first and second comparator means, said control means comprising means for enabling receipt of the output signals of the first and second comparator means at respectively different times relative to said atrial stimulation pulses and said ventricular stimulation pulses.

9. An implantable cardiac stimulator as claimed in claim 1 wherein said cardiac signals have an amplitude, and wherein said detector comprises:

comparator means for comparing the amplitude of said cardiac signals to a reference level and for emitting an output signal if the amplitude of said cardiac signals exceeds said reference level;

switch means for selectively supplying one a predetermined atrial reference level or a predetermined ventricular reference level to said comparator means as said reference level; and wherein said implantable cardiac stimulator comprises control means connected to said pulse generator said comparator means and said switch means for controlling said pulse generator dependent on said output of said comparator means and for operating said switch means to supply one of said atrial reference level or said ventricular reference level to said comparator means at selected times relative to said atrial stimulation pulses and said ventricular stimulation pulses.

10. An implantable cardiac stimulator as claimed in claim 1 wherein said cardiac signals have an amplitude, and wherein said detector comprises:

variable gain amplifier means supplied with said cardiac signals for amplifying said cardiac signals with a selected gain for producing amplified cardiac signals;

comparator means, supplied with said amplified cardiac signals, for comparing the amplitude of said amplified cardiac signals to a single reference level and for emitting an output signal if the amplitude of said amplified cardiac signals exceeds said single reference level;

and wherein said implantable cardiac stimulator comprises control means, connected to said pulse generator, said variable gain amplifier means and said comparator means for controlling said pulse generator dependent on the output of said comparator means and for setting said gain of said variable gain amplifier means to respectively different gains at different times relative to said atrial stimulation pulses and said ventricular stimulation pulses.

* * * * *